United States Patent [19]

Brignola

[11] 4,244,378
[45] Jan. 13, 1981

[54] PRESSURE RESPONSIVE ONE-WAY VALVE FOR MEDICAL SYSTEMS

[75] Inventor: Dominic J. Brignola, Phoenixville, Pa.

[73] Assignee: The West Company, Phoenixville, Pa.

[21] Appl. No.: 910,760

[22] Filed: May 30, 1978

[51] Int. Cl.³ .............................................. A61B 5/14
[52] U.S. Cl. ................................... 128/766; 128/764; 128/274; 128/218 NV; 137/843
[58] Field of Search ................. 128/2 F, DIG. 5, 274, 128/218 NV, 214 R, 214 C; 137/843

[56] References Cited

U.S. PATENT DOCUMENTS

| | | | |
|---|---|---|---|
| 605,549 | 6/1898 | Johansson | 137/843 X |
| 723,042 | 3/1903 | Schwerin | 128/274 X |
| 3,021,841 | 2/1962 | Burke | 128/214 C |
| 3,807,445 | 4/1974 | McPhee | 137/843 X |
| 3,848,579 | 11/1974 | Villa-Real | 128/2 F |
| 3,874,367 | 4/1975 | Ayres | 128/2 F |
| 3,886,937 | 6/1975 | Bobo et al. | 128/214 R |
| 3,889,710 | 6/1975 | Brost | 137/843 X |
| 4,005,710 | 2/1977 | Zeddies et al. | 128/214 R |
| 4,141,379 | 2/1979 | Manske | 128/214 R X |

Primary Examiner—Kyle L. Howell
Attorney, Agent, or Firm—Eugene E. Renz, Jr.

[57] ABSTRACT

A valve assembly comprising a housing having a valve chamber, an inlet at one axial end of the valve chamber and an outlet at the opposite axial end of the valve chamber. A rib surrounds the inlet opening in the chamber. A valve element is mounted in the chamber comprising a generally disc-like body portion having a top face and a bottom face, and a plurality of pedestals depending from the bottom face. The top face of the valve element confronts the rib and the terminal ends of said legs abut the opposite axial end wall of the valve chamber. The axial height of the valve element is slightly greater than the axial depth of the valve chamber between the rib and opposite axial end wall so that a predetermined pressure at the inlet greater than pressure at the outlet is required to open the valve element. The peripheral wall of the valve chamber has at least one flow passage to permit flow from the inlet to the outlet when the valve element is lifted by a predetermined pressure at the inlet.

3 Claims, 20 Drawing Figures

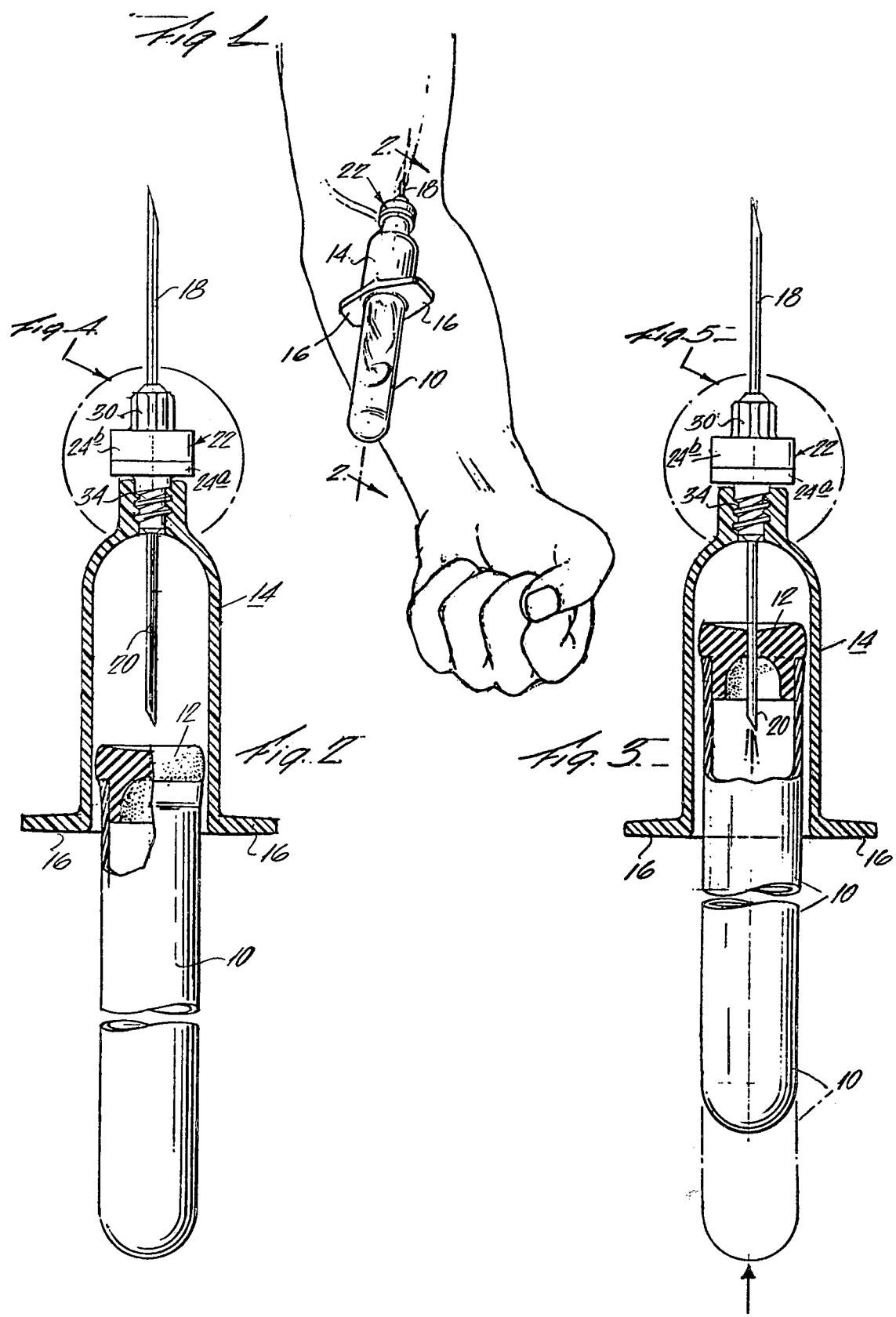

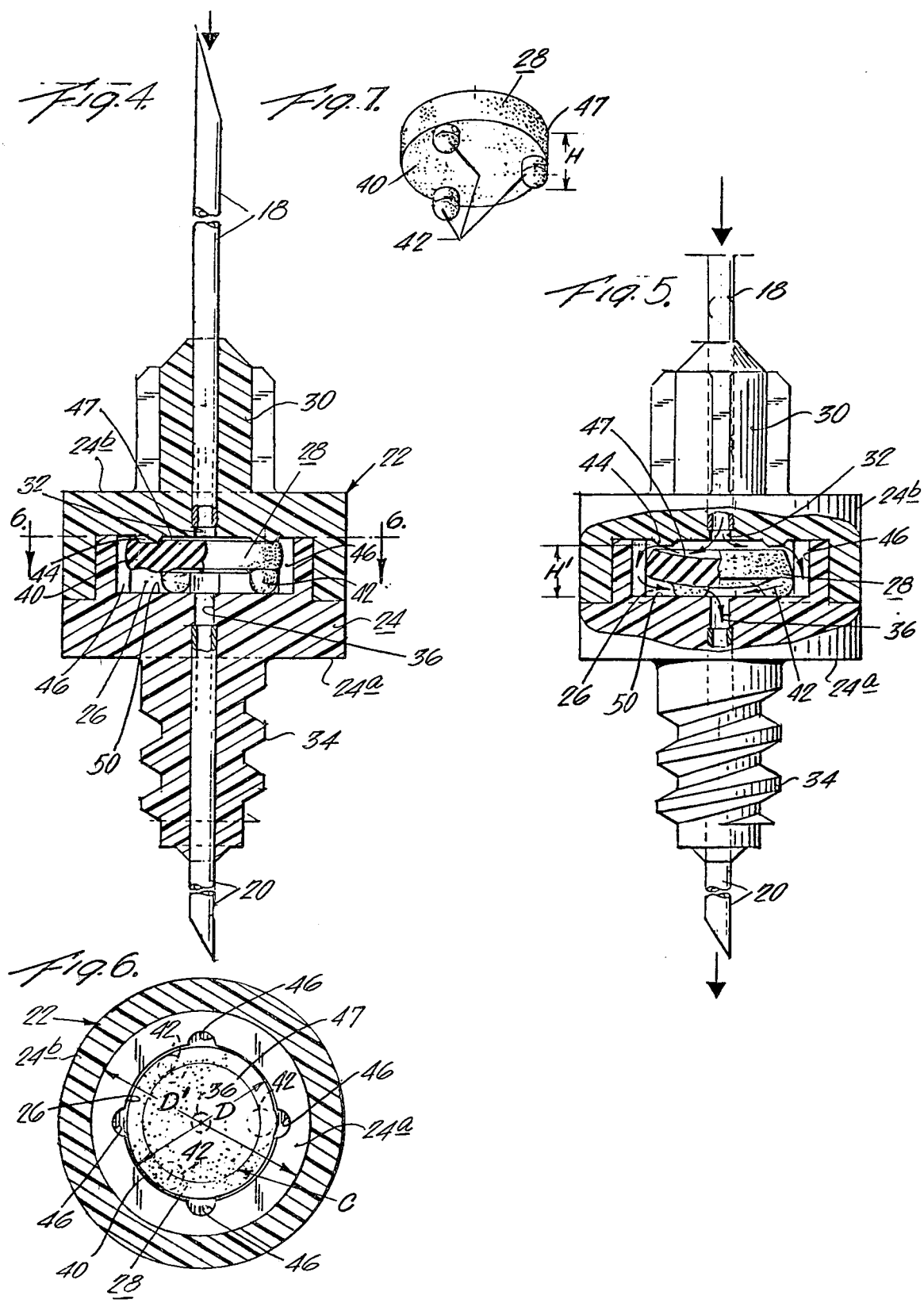

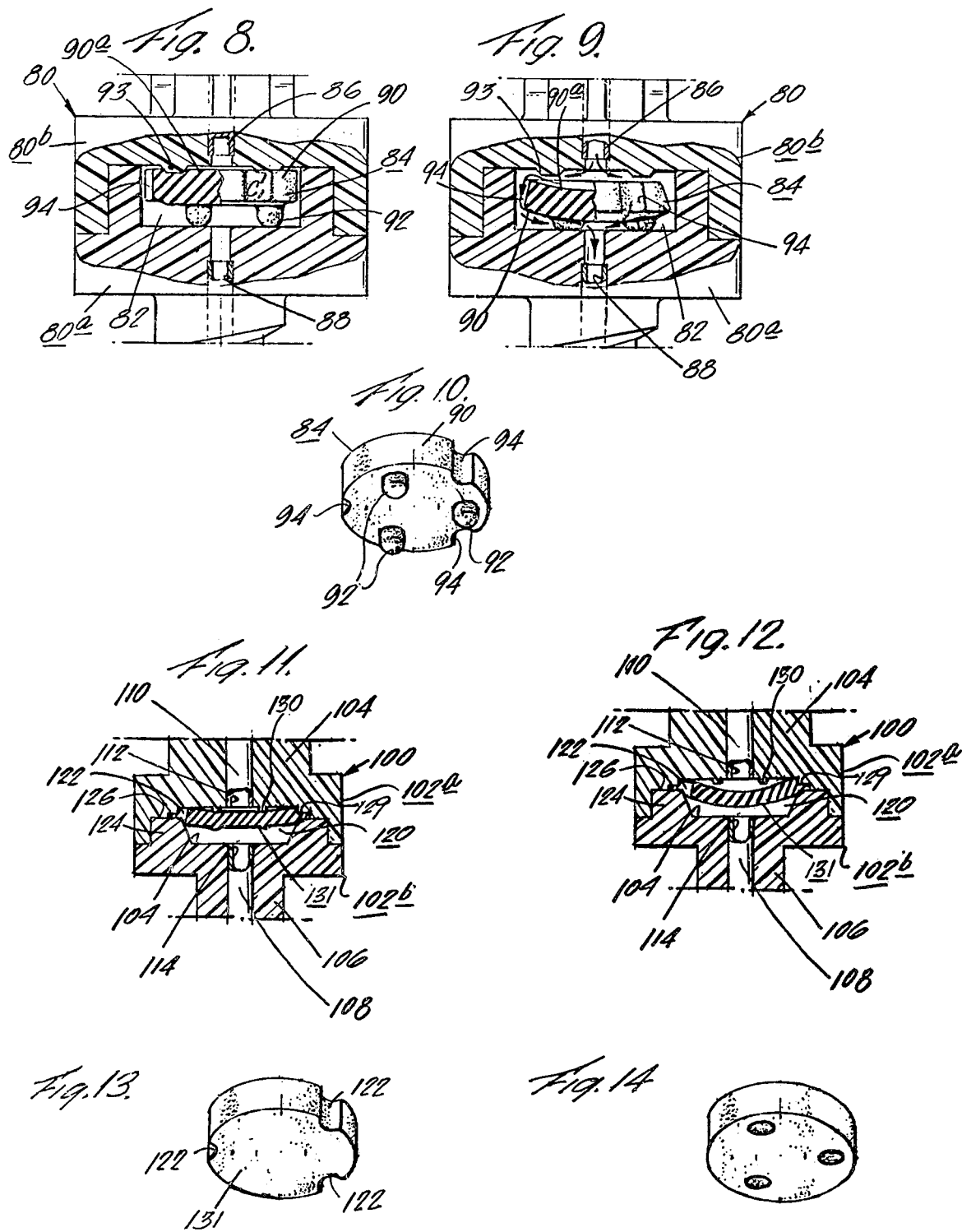

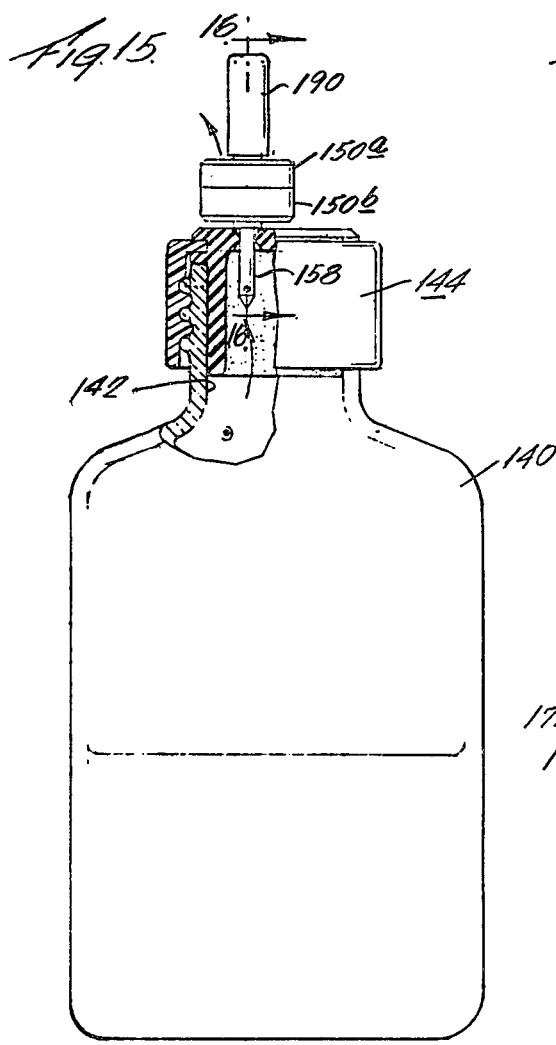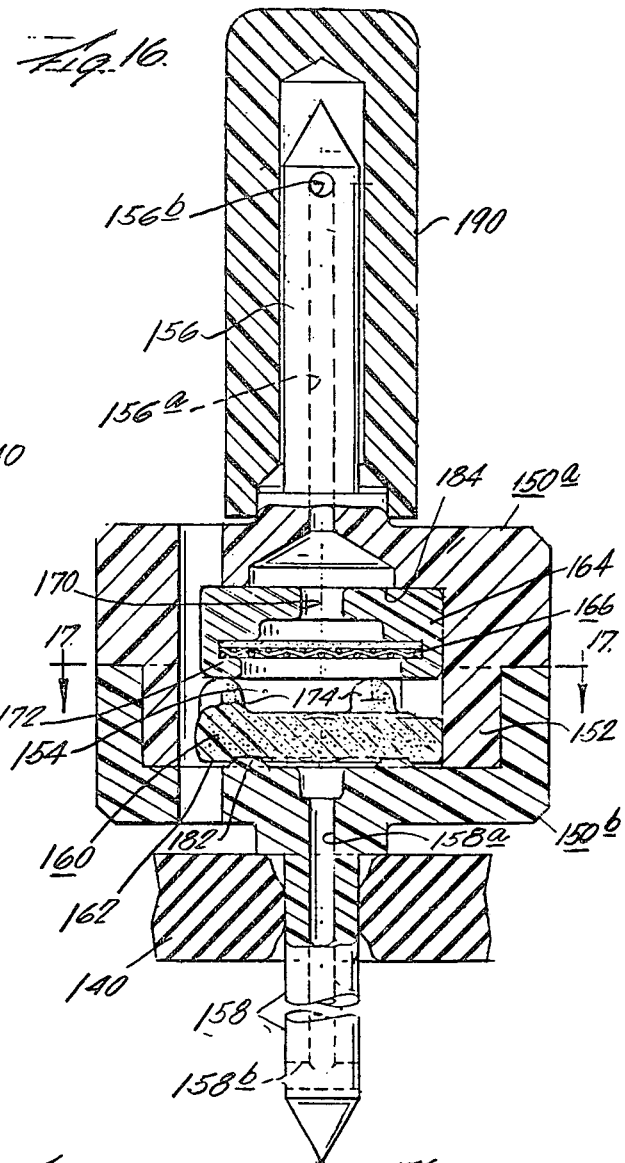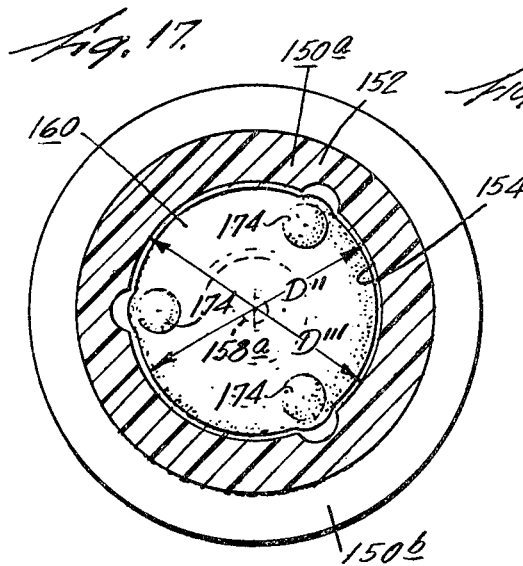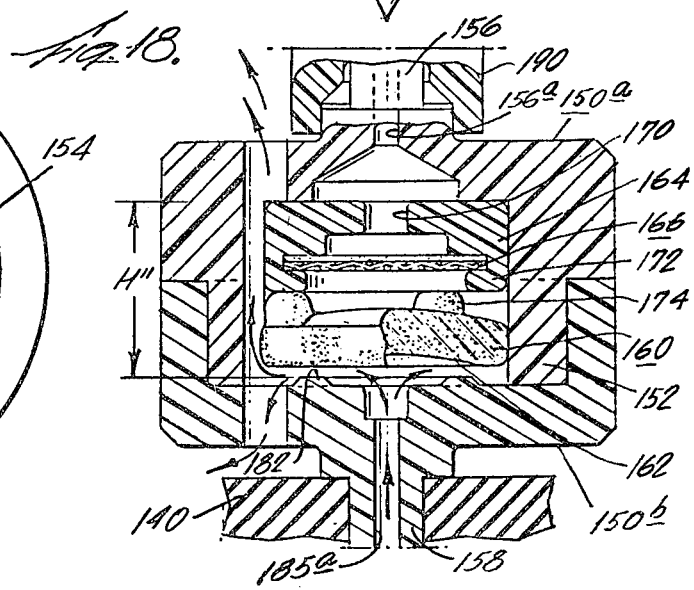

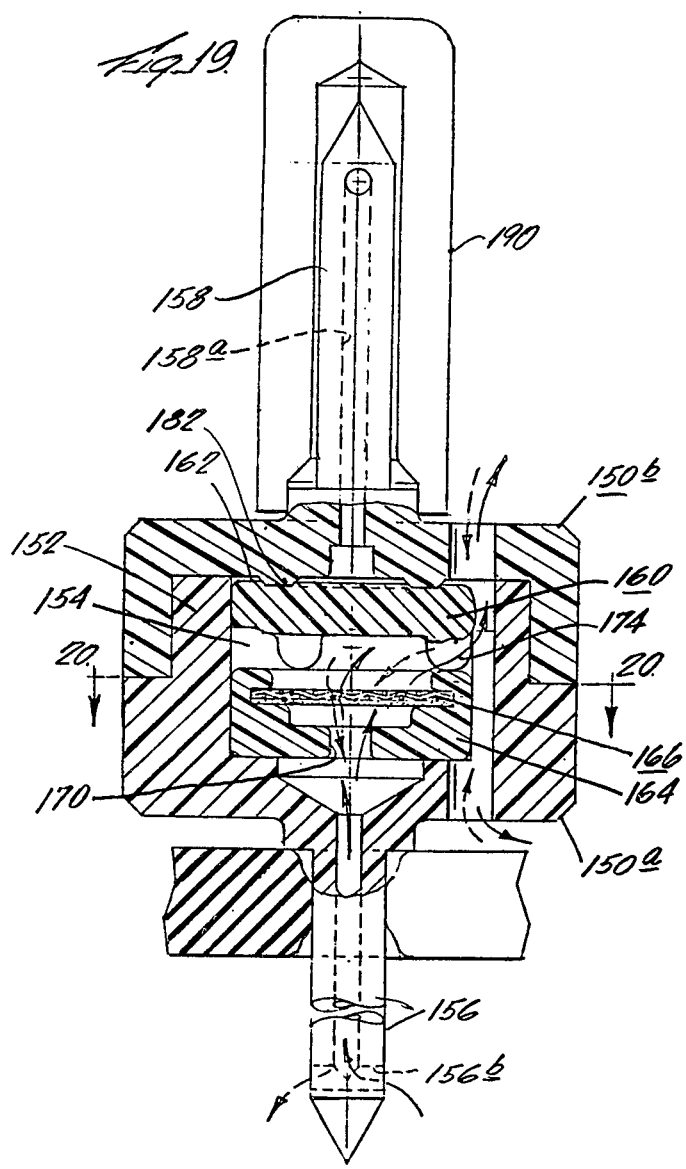
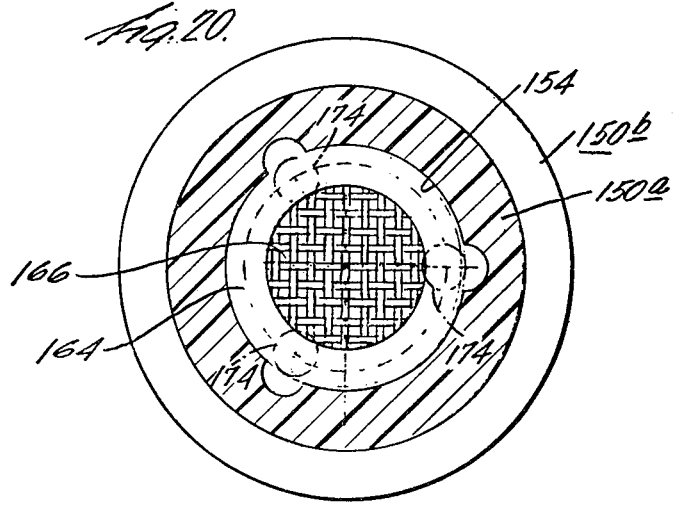

PRESSURE RESPONSIVE ONE-WAY VALVE FOR MEDICAL SYSTEMS

BACKGROUND OF THE INVENTION

The present invention relates to a one-way valve. More particularly the invention relates to a one-way valve which is characterized by novel features of construction and arrangement so that it is very sensitive to pressure differentials and which is extremely reliable in operation. For these reasons it is particularly useful in certain types of surgical and laboratory systems, such as blood collecting systems.

In accordance with some typical prior art techniques for drawing blood samples, a syringe consisting essentially of a barrel with a plunger and a needle at one end is used. The nurse or technician prepares the patient in the conventional fashion by applying a tourniquet and when the vein is raised simply inserts the needle into the vein and draws the plunger rearwardly to create a vacuum which then draws blood into the syringe. The nurse then expels the contents of the syringe into a tube which is sealed and then is ready for further processing. This system has certain disadvantages and drawbacks. For example, if the syringe plunger is pulled back roughly or with too much pressure, currents are created in the blood which break up the red blood cells. Furthermore, it has been observed that if the blood sample is transferred to the sampling vial too rapidly, hemolysis can result. This in turn can cause a sharp rise or fall in test values. Additionally where plural samples are required, separate syringe assemblies are used requiring repuncturing of the vein which is undesirable and may result in aneurysm. The syringe method also presents the danger of injecting air into the patient which can cause undesirable clotting.

In other instances the blood sampling device comprises a cup-shaped holder which mounts a double ended needle, one needle projecting exteriorly of the holder which the nurse inserts in the vein, the other needle interiorly of the holder to receive a vacuum tube for collecting the blood sample. The inner needle is covered with a rubber sheath or shield which collapses accordion-style when the stopper of the vaccum tube is pierced to withdraw a first sample and which when the vacuum tube is removed reseals the needle. It has been found that these systems are only partially effective since the sheath does not always retract to a position to close the needle and stop the flow of blood from the vein. In these systems there is the possibility of return blood flow from the vacuum tube to the patient if the patient's blood pressure fluctuates and drops below that in the vacuum tube. Return flow can be dangerous since it may contain entrained unsterile matter or drug additives from the vacuum tube.

The one-way valve assembly of the present invention has particular application in blood collecting systems of this type and operates in a manner to preclude flow through the needle until the vacuum tube has been applied to the inner needle and closes immediately to prevent further blood flow when a filled tube is removed. The valve also responds to patient blood pressure and closes rapidly when veinal pressure drops below pressure in the vacuum tube thereby eliminating return of possibly contaminated blood from the vacuum tube to the patient. The valve precludes injection of air into the vein, minimizes loss of blood and controls flow in a manner minimizing damage to the blood cells.

The valve of the present invention has other useful applications in other medical and related fields such as venoclysis equipment and in systems for cultivating organisms.

Flow control valves for use in surgical apparatus or the like or in the administration of injection fluids are not new per se. Examples of valve systems in applications of this type are described in Zeddies et al U.S. Pat. No. 4,005,710; Cox U.S. Pat. No. 3,098,779; Nehring U.S. Pat. No. 3,469,572; German Pat. No. 2,349,996; Burke U.S. Pat. No. 3,021,841; Martinez U.S. Pat. No. 2,784,733; Beacham U.S. Pat. No. 2,844,147; and Abbott U.S. Pat. No. 2,538,662.

Of the patents listed above the Zeddies Pat. No. 4,005,710 is of particular interest. The Zeddies Patent shows a valve designed for use in an administration set consisting essentially of a conventional parenteral solution container with an air vented drip chamber connected through a tubing system including a Y-type injection site to a hyperdermic needle. The valve normally is open to permit flow of parenteral solution. If a second solution is introduced at a higher pressure than the parenteral solution, the valve is displaced to close flow of the parenteral. The valve is a disc-shaped element which has a plurality of projections depending from one face thereto. When the valve element is displaced in one direction for example downwardly, fluid flows from the inlet to the outlet through the spaces between the projections. In the raised position the valve normally seals the inlet opening and this condition exists when, for example, a second solution is introduced in the system through the inlet at a greater pressure than the pressure exerted by the fluid in the inlet. The valve height is substantially smaller than the axial depth of the cavity in which it is mounted to permit substantial axial movement when it is actuated between extreme limit positions and therefore there is a time lag when the valve moves between the limit positions.

The valve assembly of the present invention differs from the prior art and comprises a disc-like valve element made of a resilient flexible material such as rubber which has a plurality of circumferentially spaced axially projecting pedestals or legs projecting from one face thereof. This valve element is mounted in a housing having a valve chamber and is of a slightly smaller diametric dimension so that the valve contact with the sidewall of the valve chamber is limited. The housing has an inlet to the space above the upper face of the valve and an outlet at the opposite axial end of the valve cavity. The dimensional relationships and the valve chamber are such that the valve element is under predetermined compression in its normally closed position requiring a predetermined pressure at the inlet to unseat the valve element to permit flow from the inlet past the valve to the outlet. When used in a blood collecting system, the valve element remains closed at normal veinal pressures. In the preferred embodiment of the invention, a pair of cannulas project from the housing, one communicating with the inlet and the other with the outlet. The valve chamber has in the preferred arrangement a series of axial passages which are circumferentially spaced to define flow paths when the valve is displaced by either a pressure build up in the inlet which exceeds the pressure on the outlet side or a drop in pressure at the outlet side compared to the pressure at the inlet side. In applications where this assembly is used to draw blood from a vein, the nurse may insert one cannula or needle into the vein and by reason of the slight compression of the valve in the valve chamber, the inlet opening remains sealed. Now when it is desired to draw a sample, a vacuum tube having a pierceable stopper is engaged over the outlet needle or cannula which reduces the pressure sufficiently in the outlet chamber to effect downward deflection of the valve permitting flow of blood from the vein to the collection tube. It is noted that as the tube fills and the pressure balances, the valve closes. In this manner the nurse may remove the filled vacuum tube and insert another for additional withdrawal of blood without removing the device from the vein of the patient. If during the blood sampling cycle, patient blood pressure drops, the valve element closes rapidly thereby preventing flow of blood which may be contaminated back through the system into the patient.

A valve of the present invention, therefore, provides certain advantages over the prior art valves which may be broadly characterized as floating valve arrangements. This contrasts with the valve of the present invention wherein the valve element is under compression in the valve chamber so that the pressure differential required to open the valve may be controlled within very precise and controlled limits. Furthermore, the present invention provides the advantage of providing an effective seal in its normal closed position.

BRIEF DESCRIPTION OF THE DRAWINGS

These and other objects of the present invention and the various features and details of the operation and construction thereof are hereinafter more fully set forth with reference to the accompanying drawings wherein:

FIG. 1 is a perspective view of a blood collecting device incorporating a valve assembly constructed in accordance with the present invention;

FIG. 2 is an enlarged side elevational view partly in section showing the blood collecting device;

FIG. 3 is a view similar to FIG. 2 showing the device in an operative position;

FIG. 4 is an enlarged sectional view of the encircled area of FIG. 2 showing the internal construction of a valve for a blood collection device;

FIG. 5 is a side elevation view partly in section of the encircled area of FIG. 3 showing the valve element in an actuated position permitting flow from the inlet to the outlet;

FIG. 6 is a sectional view taken on lines 6—6 of FIG. 4;

FIG. 7 is a perspective view of the valve element;

FIG. 8 is an enlarged fragmentary view partially in section transverse of a modified form of one-way valve assembly in accordance with the present invention;

FIG. 9 is an enlarged fragmentary view partially in section of the assembly shown in FIG. 8 in an operative position;

FIG. 10 is a perspective view of the valve element of the assembly shown in FIG. 9;

FIG. 11 is an enlarged fragmentary view partially in section of an additional modified form of one way valve assembly in accordance with the present invention;

FIG. 12 is an enlarged fragmentary view partially in section of the assembly shown in FIG. 11 in an operative position;

FIG. 13 is a perspective view of the valve element shown in FIGS. 11 and 12;

FIG. 14 is a perspective view of a modified form of valve element that can be used in the assembly shown in FIGS. 11 and 12;

FIG. 15 is a side elevational view partly in section of a culture unit with a one-way relief valve assembly in accordance with the present invention;

FIG. 16 is an enlarged sectional view through the relief valve showing the internal construction thereof taken on line 16—16 of FIG. 15;

FIG. 17 is a sectional view taken on lines of FIG. 16;

FIG. 18 is a fragmentary sectional view similar to FIG. 16, showing the valve in a raised position;

FIG. 19 is a transverse sectional view with the relief valve inverted for aerobic uses; and FIG. 20 is a sectional view taken on lines 20—20 of FIG. 19.

DESCRIPTION OF THE PREFERRED EMBODIMENTS

The valve assembly of the present invention has particular application in blood collecting systems and the operation thereof may be best understood in connection with a typical system illustrated in FIGS. 1–5 inclusive of the drawings. The blood collecting system as illustrated includes a vacuum tube or vial 10 having a rubber stopper 12 fitted in the open end thereof. Typically a vacuum is drawn on the vial and then the stoppers are assembled so that the interior is at sub-atmospheric pressure. These vials are usually referred to as "vacuum collecting tubes". As discussed above these collecting tubes are used in conjunction with a double-pointed needle mounted in a generally cup-shaped holder designated by the numeral 14. This holder 14 has finger grip portions 16 at its open end and is of an enlarged diameter to receive the vacuum tube therein in the manner illustrated in FIG. 3. In using this system, therefore, the nurse or technician partially assembles the vacuum tube to the inner needle 20 inserts the outer needle 18 into the vein of the patient and then simply pierces the inner needle 20 completely through the diaphragm portion of the stopper 12 by gentle pushing it axially. As explained in detail below, this opens the valve element in the valve assembly at the juncture of the needles and permits the flow of blood to the vacuum tube.

Considering now in more detail the internal construction and arrangement of a valve assembly in accordance with the present invention and with reference to FIGS. 4–7, the assembly is generally designated by the numeral 22 and comprises a housing or casing 24 having a valve chamber 26 therein and a disc-like valve element 28 actuatable between a closed position (FIG. 4) blocking flow between the inlet side and the outlet side and an open, depressed position (FIG. 5) permitting flow from the inlet to the outlet side around the valve element 28. In the present instance the housing or casing 24 is a two-piece assembly comprising inner and outer sections 24a and 24b which may be assembled together in the manner shown by a press fit. The outer housing section 24b has a hub support 30 which mounts the needle 18 insertable into the vein of the patient communicating at its inner end with an inlet opening 32 to the valve chamber 26. The inner housing section 24a has an externally threaded hub 34 which mounts the needle 20 communicating through an outlet port 36 with the valve chamber. The threaded hub permits assembly to the holder in the manner illustrated in FIGS. 2, 3. In this manner the valve assembly may be made as a disposable assembly.

In the embodiment illustrated, the housing may be cast of a rigid plastic material and the needles which may be made of metal can be press fitted therein. Alternately the needles can be formed integrally with the housing sections. Additionally the housings may be secured in other ways, for example, by a threaded connection and provided with suitable seals to prevent leakage from the valve chamber, ultrasonic welding or a complementary bead and groove arrangement facilitating a snap fit.

The valve element as illustrated comprises a generally disc-like body portion 40 having a plurality of circumferentially spaced legs or pedestals 42 depending from the lower face thereof. In the embodiment illustrated three legs are shown.

The valve chamber 26 is a generally cylindrical cavity having at one axial end a depending rib or flange 44 which surrounds the inlet opening 32 and as illustrated in FIGS. 4, 5 is adapted to press against the upper face of the valve element in the closed position of the valve. The sidewall of the chamber is provided, in the present instance, with four (4) equispaced cut outs 46 defining flow passages around the valve element. As illustrated the valve element is preferably of a diameter D slightly smaller than the diameter D' of the valve chamber to permit limited movement. Additionally the axial height H of the valve element measured from its top face 47 to the terminal ends of the legs 42 is slightly greater than the axial height H' of the valve chamber between the annular rib 44 and the bottom wall 50 of the chamber so that in the normal position there is a good sealing engagement of the rib with the upper face of the valve surrounding the inlet opening.

Preferably the annular rib 44 engages the top face 47 of the valve chamber body along a circular line or area C passing through the center of each of the legs 42. In this manner the precompression of the valve element may be controlled more precisely to provide the desired pressure at the inlet to open the valve. By this construction the valve normally seats in a closed position and remains seated even when a predetermined pressure slightly above atmospheric is exerted at the inlet. This occurs, for example, when the vein needle is inserted and veinal pressure exists at the inlet side of the valve element. Now when the vacuum tube is inserted over the needle at the other end, the differential pressure is such that the valve body is deflected downwardly to displace the upper face 47 from the annular rib 44 surrounding the inlet opening thereby permitting flow past the upper face of the valve through the axial flow channels in the valve chamber and through the space between the lower face of the valve and the legs to the outlet opening and then through the needle into the vacuum tube. Upon drawing a predetermined given volume of blood in the vacuum tube, the pressure now balances to a point where the valve automatically closes. The vacuum tube may then be removed and if another sample is required, a new empty tube can simply be inserted over the vacuum needle end of the valve assembly.

It is to be understood that various parameters determine the opening pressure differential for the valve. The following example, however, has been found to be preferred relative relationships of the valve element and the chamber for use in a blood collecting system.

Valve Element Diameter (D)—0.203 inches
Valve Chamber Diameter (D')—0.210 inches
Valve Element Axial Height (H)—0.080 inches
Valve Body Thickness—0.040 inches
Axial Height of the Legs—0.040 inches
Valve Chamber Axial Height (H')—0.075 inches There is illustrated in FIGS. 8–10 a modified embodiment of the valve assembly described above. The general construction arrangement, and operation are generally similar to that described above. Thus the valve assembly includes a casing or housing 80 consisting of interfitting housing sections 80a, 80b, a valve chamber 82 and a valve element 84 in the chamber. The housing mounts a pair of needles 86, 88 at opposite ends which communicate with the valve chamber at inlet and outlet portions of the valve chamber.

In the present instance the valve element 84 comprises a disc-like body portion 90 and a plurality of pedestals or legs 92 depending from the lower face thereof and to this extent is generally similar to the valve element described above. However, in the present instance the body portion 90 is provided with a series of circumferentially spaced cut outs 94 which define the flow passages. In this instance the sidewall of the valve chamber is cylindrical and the valve body snugly engages the sidewall of the valve chamber except at the cut out locations.

Preferably the annular rib 93 engages the top face 90a of the valve chamber body along a circular line or area $C_1$ passing through the center of each of the legs 92.

The valve assembly operates in essentially the same manner as the valve described above. Thus, the valve element is normally seated in a closed position illustrated in FIG. 8 wherein the flow path from the inlet opening to the discharge opening is sealed off by engagement of the circumferential rib 93 against the upper face of the valve body at a point spaced radially inwardly from the arcuate cut outs defining the flow passages around the valve element. Now when there is a predetermined pressure differential between the inlet and the outlet opening, for example, when used in applications to draw blood from a patient, the pressure on the upper face of the valve body deflects the valve downwardly to permit flow past the circumferential rib to the flow passages in the periphery of the valve body and through the space between the legs and the lower face of the valve body to the discharge outlet.

This arrangement provides several functional advantages particularly in blood collecting systems. For example, when the vacuum tube is full, the valve automatically closes precluding entry of air to the vein of the patient. This is important since air can cause clotting which can be fatal to the patient. Further since there is no further flow of blood to the vacuum collector needle 20, there is less patient blood loss which is desirable. Furthermore, the other parts of the system are not contaminated with blood which in addition to being unsightly can in some instances frighten the patient. Since the needle assembly can remain in a fixed position in the vein the danger of aneurysms is practically eliminated.

There is illustrated in FIGS. 11–14 another embodiment of flow control valve in accordance with the present invention generally designated by the numeral 100. The valve comprises a pair of housing sections 102a and 102b which in the assembled relation define an enclosed valve chamber 104. Each housing section as illustrated has a hub support 104, 106 which mounts a needle or cannula 108, 110. The needle 110 terminates at its inner end in an inlet opening 112 and needle 108 has an outlet opening 114 at its inner end. A disc-like valve element 120 having a series of cut outs 122 in its outer periphery which define flow passages is mounted in the valve chamber.

The housing section 102a has a circumferentially extending annular flange 124 which seats on a shoulder 126 in the housing section 102b to support the valve element in the position shown. The inner face of the housing section 102a is of stepped configuration defining a shelf 130 for the valve element and an annular rib 129 surrounding the inlet opening which projects axially inwardly a slightly greater extent than the shelf 129 so that it engages the inner face of the valve element and applies a slight compression so that the valve only opens at a predetermined pressure at the inlet.

FIG. 14 shows a modified form of valve element which as illustrated is also disc-like and has a series of openings 131 spaced inwardly from the outer peripheral edge of the disc which define the flow passages. These openings are located radially outwardly of the annular rib 130 to prevent flow from the inlet to the outlet when the valve is seated against the rib and is slightly compressed thereby.

Considering now briefly operation of the valve and assuming that it is used in a blood collection system, when the needle 110 is inserted into the vein, the vein remains closed (FIG. 11). Now when the needle 108 pierces the stopper in a vacuum tube to create a lower pressure at the outlet opening the pressure differential is such to deflect the valve element away from the rib 130 (FIG. 12) permitting flow of blood from the inlet through the flow passages 122 to the outlet 114 and then into the vacuum tube. When the tube is filled and the pressures balance, the valve element closes.

The valve assembly of the present invention has other useful applications. For example, it may be used in conjunction with enclosed vessels or the like used by microbiologists to cultivate organisms. A typical vessel is that illustrated in FIG. 15 which comprises a candle jar 140 having a threaded opening 142 with a typical closure including a stopper 144 made of a resilient material such as rubber. In a typical process the cultures are placed in the container and a culture medium added and then the candle jar is sealed with the closure. During the incubation period, certain chemical reactions take place which generate gases in the culture jar which in some instances can reach a level causing explosion of the jar unless vented. Venting, however, must be done in a controlled manner since these processes usually involve organisms falling into two broad categories, anaerobes which do not require oxygen or that grow only in the complete absence of oxygen, and aerobes, that is organisms which do require oxygen. The present invention provides a venting unit which is useful for both types of systems.

Considering now the structural details and arrangement of the valve in accordance with the present invention, the valve assembly comprises a two-piece housing 150a 150b, 150a having a central body portion 152 which has a valve chamber 154 defined therein, each housing section in the present instance has formed integrally therewith a hollow cannula or spike 156, 158 which terminates in a pointed tip to penetrate the diaphragm of the closure. As illustrated each cannula has a central bore 156a, 158a with a cross bore 156b, 158b at its outer terminal end providing communication with the interior of the valve chamber and the interior of the container when it is mounted therein in a manner illustrated in FIG. 15. The valve chamber mounts therein a valve element 160 having its upper flat face 162 engageable over the central port 158a to one cannula 158 and also mounting therein a disc-like supporting element 164 for a filter 166. The filter support disc 164 has an opening 170 to provide a flow path from the bore 156a of cannula 156 to the valve chamber and a depending outer flange 172 against which the legs 174 of the valve element abut.

The valve chamber, the filter support element and valve element are of a predetermined dimensional relationship so that the valve element seats against the annular rib 182 surrounding the inner end of cannula bore 158a and a predetermined pressure greater than atmosphere is required to unseat the valve element. Thus the axial height H" of the valve chamber from the end wall 184 adjacent the cannula bore inlet 156a is preferably smaller than the combined axial height of the filter support and valve element. Further the diameter D" of the valve elements is preferably slightly smaller than the diameter D''' of the valve chamber.

Considering now the use of the one way relief valve of the present invention, after the culture has been prepared in the candle jar and the closure applied, in the event the culture being grown is anaerobic, the valve assembly is inserted with the inner cannula 158 engaging interiorly of the container which as illustrated in FIG. 15 prevents ingress of oxygen to the interior of the candle jar. Now during the incubation period if the pressures develop internally above a predetermined level, the valve unseats to permit escape and thereby obviates any danger of explosion. When the pressure balances again, the valve closes and seals the environment of the candle jar from ingress of outside air. Now if the culture being prepared is aerobic, the device is simply inverted so that the transfer spike or cannula 156 extends through the diaphragm. This position is illustrated in FIG. 19. This establishes free flow and communication in both directions through the filter which prevents ingress of any bacteria or other organisms in the environment which may contaminate the culture in the enclosed environment in the candle jar. Since the interior of the valve is closed from view, each transfer spike may be color coded to indicate aerobic or anaerobic use. Alternatively, the cover element 190 for each cannula may be so color coded. The cover element also adds a safety feature protecting the hand of the user when puncturing the stopper with the exposed spike of the valve assembly.

What is claimed is:

1. A valve assembly comprising a housing having a valve chamber, an inlet at one axial end of said valve chamber, a rib depending from said one axial end face circumscribing said inlet and spaced radially outwardly therefrom, an outlet at the opposite axial end of said valve chamber, a disc-like valve element mounted in said chamber comprising a generally disc-like body portion having a top face and a bottom face, and a plurality of pedestals depending from the bottom face, the top face confronting said rib and the terminal ends of said legs abutting said opposite axial end wall of said valve chamber, said annular rib engaging the top face of said body portion in a circular plane extending through the center of said pedestals, the axial height of said valve element being slightly greater than the axial depth of said valve chamber between said rib and said opposite axial end wall and means defining a least one flow passage adjacent the periphery of said valve element, permitting flow from between said inlet and outlet at a predetermined pressure differential to displace said top face of the valve element away from said rib.

2. A valve assembly as claimed in claim 1 including a cannula projecting from one end of said housing in communication with said inlet and a cannula projecting from the opposite end of said valve housing communicating with said outlet.

3. A valve assembly as claimed in claim 1 wherein said flow passage is defined by a plurality of circumferentially spaced cut outs in the peripheral wall of said valve chamber.

* * * * *